(12) United States Patent
Ozden

(10) Patent No.: US 8,527,292 B1
(45) Date of Patent: Sep. 3, 2013

(54) MEDICAL DATA ANALYSIS SERVICE

(75) Inventor: Banu R. Ozden, New York, NY (US)

(73) Assignee: Smartmc, LLC, New York, NY (US)

(*) Notice: Subject to any disclaimer, the term of this patent is extended or adjusted under 35 U.S.C. 154(b) by 1273 days.

(21) Appl. No.: 11/475,652

(22) Filed: Jun. 26, 2006

Related U.S. Application Data

(60) Provisional application No. 60/696,355, filed on Jul. 1, 2005.

(51) Int. Cl.
- G06Q 10/00 (2012.01)
- G06Q 50/00 (2012.01)
- G06Q 40/00 (2012.01)
- G07B 17/00 (2006.01)
- G07F 19/00 (2006.01)

(52) U.S. Cl.
USPC .................................. 705/2; 705/4; 705/30

(58) Field of Classification Search
None
See application file for complete search history.

(56) References Cited

U.S. PATENT DOCUMENTS

| | | | |
|---|---|---|---|
| 5,970,463 A | 10/1999 | Cave et al. | |
| 6,061,657 A | 5/2000 | Whiting-O'Keefe | |
| 6,324,516 B1 | 11/2001 | Shults et al. | |
| 6,341,265 B1 | 1/2002 | Provost et al. | |
| 6,370,511 B1 | 4/2002 | Dang | |
| 6,551,266 B1* | 4/2003 | Davis, Jr. | 604/6.09 |
| 6,655,583 B2 | 12/2003 | Walsh et al. | |
| 6,687,685 B1 | 2/2004 | Sadeghi et al. | |
| 6,826,536 B1 | 11/2004 | Forman | |
| 6,882,983 B2 | 4/2005 | Furphy et al. | |
| 6,915,254 B1 | 7/2005 | Heinze et al. | |
| 6,973,441 B1 | 12/2005 | Jaggi | |
| 2002/0026332 A1* | 2/2002 | Snowden et al. | 705/3 |
| 2003/0046112 A1* | 3/2003 | Dutta et al. | 705/3 |
| 2004/0088192 A1* | 5/2004 | Schmidt et al. | 705/3 |
| 2004/0117215 A1* | 6/2004 | Marchosky | 705/3 |
| 2004/0243433 A1* | 12/2004 | Akin et al. | 705/2 |
| 2005/0137912 A1* | 6/2005 | Rao et al. | 705/4 |
| 2005/0261944 A1* | 11/2005 | Rosenberger | 705/4 |
| 2006/0095298 A1* | 5/2006 | Bina | 705/2 |
| 2006/0259325 A1* | 11/2006 | Patterson | 705/2 |

OTHER PUBLICATIONS

"Yahoo! Health," Web page printed from health.yahoo.com on Jun. 26, 2006 (pp. 1-2).

"WebMD Health Manager," Web page printed from healthmanager.webmd.com on Jun. 26, 2006.

"Medical Bill Software—Quicken Medical Expense Manager," Web page printed from quicken.intuit.com on Jul. 1, 2005 (pp. 1-3).

(Continued)

*Primary Examiner* — Jason M Borlinghaus

(74) *Attorney, Agent, or Firm* — Treyz Law Group

(57) ABSTRACT

A medical data analysis service is provided. The service may be implemented as an on-line service using a data analysis server. The data analysis server may maintain patient databases and a community database. Each patient database may be populated with patient medical expense data such as medical bills from health care providers and insurance statements from insurance providers. The service analyzes the data in the databases to identify potential errors. The system detects errors in billing and insurance coverage and enables the patient to query medical expense data. The system enables patient's notes relating to these services to be easily tracked, queried and shared. The system enables a patient to derive additional knowledge from the medical expense and insurance coverage data. This knowledge can be queried by the patient. The system enables a patient to derive more knowledge from collective patient medical expense and insurance coverage data and annotations.

22 Claims, 2 Drawing Sheets

(56) References Cited

OTHER PUBLICATIONS

"Quicken Medical Expense Manager—OurFamily.mem" Web pages of screenshots printed from quicken.intuit.com on Jul. 1, 2005 (4 pages).
"Quicken Medical Expense Manager—OurFamily.mem" Web pages of screenshots printed from quicken.intuit.com on Jul. 1, 2005 (6 pages).
Jain, Anil et al. "Statistical Pattern Recognition: A Review", IEEE Transactions on Pattern Analysis and Machine Intelligence, vol. 22, No. 1, pp. 4-37, Jan. 2000.
Kuramochi, Michihiro et al. "Finding Frequent Patterns in a Large Sparse Graph". Proceedings of the 2004 SIAM International Conference on Data Mining, pp. 345-356, 2004.
Yang, Jiong et al. "Discovering High-Order Periodic Patterns", published in Knowledge and Information Systems (2004) vol. 6: pp. 243-268, Mar. 2004.
Rigoutsos, Isidore et al. "The Emergence of Pattern Discovery Techniques in Computational Biology", Academic Press, Metabolic Engineering, (2000) vol. 2, pp. 159-177, 2000.
Srikant, Ramakrishnan et al. "Mining Sequential Patterns: Generalizations and Performance Improvements", Proc. 5th Int. Conf. Extending Database Technology, EDBT, vol. 1057, pp. 3-17, 1996.
Kuromochi, Michihiro et al. "Frequent Subgraph Discovery," IEEE International Conference on Data Mining (ICDM), 2001.

* cited by examiner

MEDICAL DATA ANALYSIS SERVICE

This application claims the benefit of provisional patent application No. 60/696,355, filed Jul. 1, 2005, which is hereby incorporated by reference herein in its entirety.

BACKGROUND OF THE INVENTION

The present invention relates to services that empower patients to manage and analyze their health care data, and more particularly, to an online service that patients can use to analyze their medical expenses and associated records.

Managing medical expenses can be a daunting task for a patient. Several providers and insurance plans are typically involved in a patient's health care, so a patient must handle numerous provider and insurance statements. The possibility for error is increased by the large number of entities involved.

Health care providers and insurance providers have financial interests that are opposed to those of their patients. Health care providers use software tools to help determine how to increase revenues from the services they provide to their patients. Similarly, insurance companies use their resources to minimize the level of patient reimbursements that are made. While providers and insurers use significant resources to protect their interests and maximize their revenues, patients are often unable to ascertain what services they are paying for and whether those payments are being properly handled by their health care providers and insurance providers.

What is needed is a service to assist patients in managing their medical expenses.

SUMMARY OF THE INVENTION

The present invention provides a medical expense data analysis service that allows patients to manage their health care. The service can be used to check whether health care providers are charging a patient too much and whether and insurance providers are reimbursing a patient too little. Patients may also use the service for other health-care management tasks. For example, patients can annotate their medical records (e.g., drug side effects experienced) or store articles or to-do lists in a patient storage area maintained by the service.

The medical data analysis service of the present invention provides a patient-centric suite of tools to assist patients with medical expense management. The service helps patients analyze medical expense data such as healthcare provider statements (also sometimes referred to as healthcare provider bills or invoices) and insurance company statements (also sometimes referred to as insurance claims, insurance provider statements, explanations of benefits records, etc.).

Dealing with medical bills can be challenging, particularly for patients who have serious medical conditions. The service of the present invention helps to relieve patients from the burdens associated with managing their medical expenses. The service saves patients time, avoids cumbersome paperwork, and helps to reduce medical expenses. This allows patients to pay medical bills and to be reimbursed in a timely manner. The service checks the correctness and appropriateness of patients' medical bills and insurance coverage to identify errors.

The service may be implemented using a stand-alone program running on a personal computer or other suitable computing equipment or using an on-line architecture in which software analysis components implemented on a server (or servers). The server may be used to manage multiple patient databases. Each patient database may include patient data for a particular patient. Patients may access their databases over the internet.

Patients may provide the service with access credentials, which the service may use to obtain data from health care providers and insurance companies. Patients may subscribe to the data analysis service or may visit the data analysis service.

The service may maintain a community database. The community database may be accessed by patients who are subscribers to the service and by visiting patients (i.e., casual web users).

The community database may be used to form a repository of collective knowledge, anonymized and mined from subscribers records and enhanced with data from reputable sources (e.g., Medicare websites). Data in the community database may relate to medical expenses. For example, data in the community database may relate to insurance coverage coding and medical coding. A search engine associated with the community database may be used to enable consumers to explore this collective knowledge. If desired, the service may provide a forum for patients to post questions and to interact with other patients regarding their health care expenses. Experts can answer questions about billing and coverage.

The community database may include patient data from multiple patient databases. Data may be provided to the community database by consenting patients. To preserve anonymity, the data from each patient may be anonymized before it is stored in the community database. Aggregating and processing patient data in the community database helps the service to identify potential errors. For example, the service can ascertain what the "reasonable and customary" charge is for a particular procedure. By gathering this information from multiple patients and their associated insurance companies, the service can alert a patient whenever that patient's insurance company's reasonable and customary levels appear out of line with community standards. Aggregating patient data in the community database also enables patients to compare annotations, e.g., drug side effects, etc.

The service can maintain the community database for the benefit of the patients without regard to the interests of their health care and insurance providers.

DETAILED DESCRIPTION OF THE PREFERRED EMBODIMENTS

The present invention relates to a service for assisting patients in analyzing their medical data. The service of the present invention may be implemented on line (e.g., on a server accessible over the internet or other suitable communications network), may be implemented using stand-alone (client) software, or may be implemented using a combination of server-based and client-based arrangements. The present discussion will describe an on-line embodiment of the medical data analysis service in which a medical data analysis server is accessed from patient web browsers as an example.

With this illustrative server-based architecture, the medical data analysis service has software running on a server. Software may also be run on equipment at a client (e.g., as a web browser plugin) and/or at health care and insurance providers (e.g., in the form of communications modules that facilitate data gathering operations). In a typical scenario, the server automatically gathers medical expense records such as doctor's bills from health care providers and insurance statements from insurance companies. This data is processed and used to populate a patient database associated with a particular patient.

The service may be used by any suitable users. Users of the service are generally people who are receiving medical care, so the users of the service are sometimes referred to as patients.

If desired, the service may be operated on a subscription basis. With this type of arrangement, some patients may be subscribers to the service, whereas other patients may be visitors to the service. Both subscribers and visitors may access the service over the internet.

Multiple patients are typically associated with the service. Each patient has a respective patient database containing their medical expense data. Other medical data (e.g., health care records, patient annotations, etc.) may also be stored in the patient databases.

The service processes and aggregates the data from the patient databases. The aggregated data is maintained in a shared database on the server. The shared database, which is sometimes referred to as a community database, contains data from multiple patients. The community database can be used to help identify errors in the way health care expenses are being handled for individual patients. When an abnormality is discovered, the appropriate patient can be notified.

Patients can log into the service through a patient portal (also sometimes referred to as a consumer portal). In a typical scenario, a given patient uses a personal computer connected to the server through the internet. The patient launches a web browser or other suitable client on their computer and accesses the service through the patient portal. The patient can use the patient portal to access their data and to perform database queries on the databases maintained at the server. Unregistered patients can either log into the service as guests or may use a visitor portal.

Figure 1:
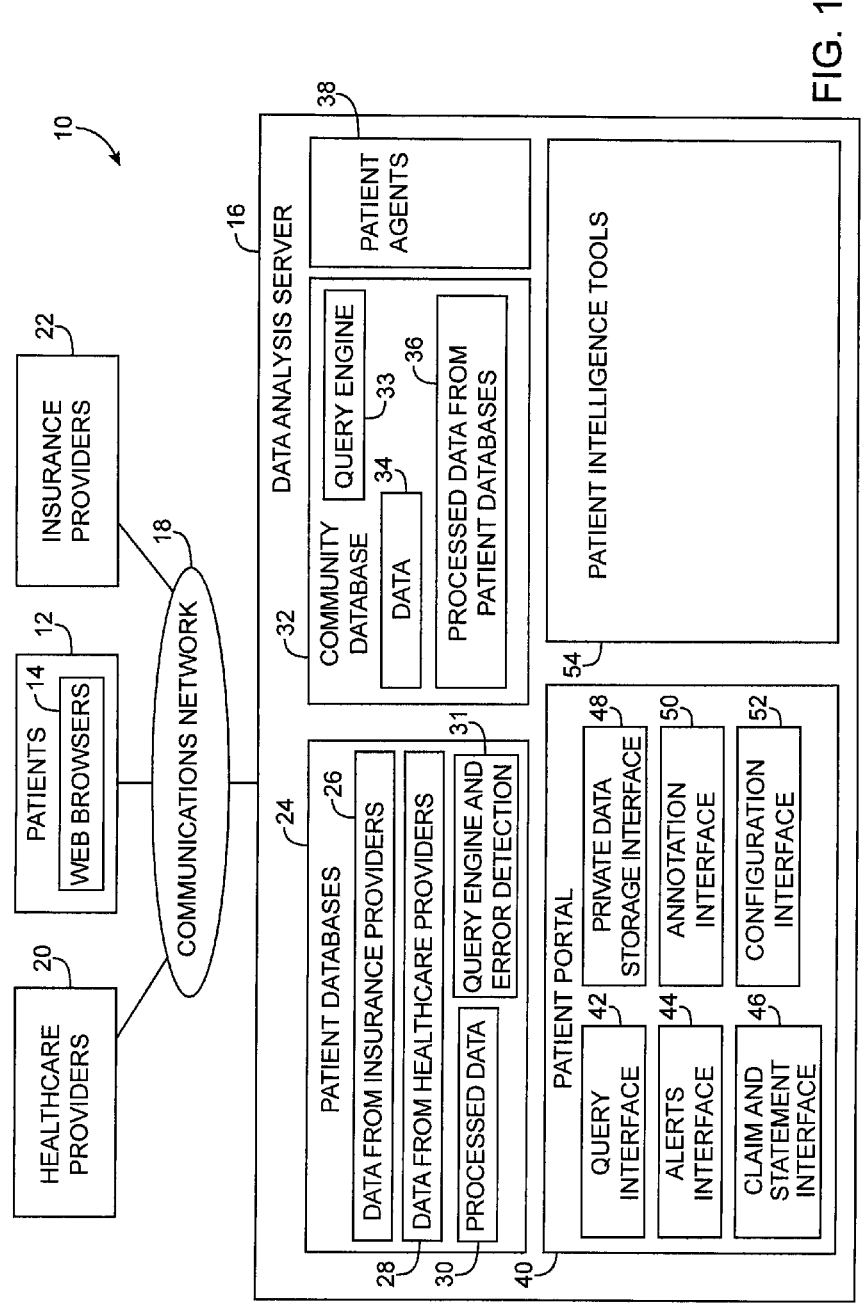
FIG. 1 is a diagram of an illustrative medical data analysis service in accordance with the present invention.

An illustrative system environment in which the medical data analysis service of the present invention can be implemented is shown in FIG. 1. In system 10, patients 12 communicate with data analysis server 16 over communications network 18. The data analysis server 16 can communicate with health care providers 20 and insurance providers 22 over network 18 if desired. Network 18 may include local area networks, wide area networks such as the internet, wired and wireless paths, or any other suitable communications network.

Entities such as health care providers 20, insurance providers 22, and patients 12 may use computers such as personal computers, mainframe computers, and workstations to handle data. If desired, smaller computing devices such as handheld computers and cellular telephones may be used where appropriate. Typically patients have personal computers in their home or office. Web browsers 14 are run on these computers. Larger health care providers 20 typically have workstation-class or mainframe computers. Smaller health care providers 20 may have personal computers. Insurance providers often use mainframe computers. Server 16 may be implemented using a personal computer, workstation, mainframe, or a cluster of one or more computers. Server 16 may be implemented at a single geographic location or may be implemented using a distributed architecture.

In general, the components of system 10 may be implemented using any suitable computing equipment. Software runs on the computing equipment of system 10 to implement the functions of the data analysis service.

Data analysis server 16 is preferably used to maintain multiple patient databases 24. In a typical scenario, each patient 12 has an associated database 24. Databases 24 can be populated with medical bills and other data 28 from health care providers 20. Databases 24 can also have data 26 from insurance providers such as insurance statements. Medical bill and insurance statement data may be provided in their entirety or portions of this data may be used when populating databases 24. The data may be entered manually by a patient (e.g., using web browser 14 and a suitable interface such as interface 46 in patient portal 40) or data may be gathered automatically. In an automatic data gathering arrangement, the patient provides server 16 with appropriate access credentials. The server 16 than uses these credentials to prove that the server 16 is authorized to obtain the data from health care providers 20 and insurance providers 22.

Patient data such as data 26 and data 28 may be processed using server 16. Processed data 30 may be maintained on a per-patient basis in databases 24, as shown in FIG. 1. The processed data may include computations performed by server 16 (e.g., when analyzing data for patterns) and may include data added by a patient (e.g., medical expense record annotations and notes).

Server 16 preferably also maintains a community database 32. The community database 32 contains processed data 36 from multiple patient databases 24. The community database 32 may also contain data 34. Data 34 may include, as an example, data derived from reliable external databases such as a Medicare database. This type of data may be used to define the interrelationships between billing and diagnostic codes (e.g., to define which treatments are authorized for a given diagnosis). Server 16 or other suitable entities may preprocess data from external databases to produce data 34.

The patient data 36 in the community database can be anonymized before it is gathered from patient databases 24, thereby helping to preserve the confidentiality of each patient. Patients can also restrict which (if any) data is to be shared with community database 32.

The community database form a repository of collective knowledge. The contents of the community database may be mined from patient records and enhanced with data from reputable sources (e.g., Medicare websites). The data in the community database may include data on insurance coverage coding and medical coding, data on reasonable and customary rates, information regarding levels of coverage that patients have received from their insurance providers, etc. Search engine 33 may be used to enable visiting patients (i.e., casual web users) to explore the contents of the community database.

If desired, the service may provide a forum for patients to post questions and to interact with other patients regarding their health care expenses. Experts can answer questions about billing and coverage.

A patient agent 38 (also sometimes called a personal assistant software module) may be associated with each patient 12 and patient database 24. The patient agents 38 can be used to store passwords and other patient credentials for use when accessing records at health care providers 20 and insurance providers 22 to populate databases 24. Agents 38 may be used to perform database queries. For example, agents 38 may query community database 32 to ascertain whether a given patient's "reasonable and customary" amount (as determined by that patient's insurance company) is in line with community standards. Database queries such as these may be performed periodically in the background or may be initiated by the patient on demand. One or more database query tools may be used to provide service subscribers and visitors to the service with the ability to query database such as databases 24 and 32. For example, query engine and error detection block 31 may be used to support database queries on database 24 and query engine 33 may be used to support database queries on database 24. The error detection capabilities of query engine and error detection block 31 may be used to help check database 24 for errors.

Patient intelligence tools 54 (also sometimes called consumer intelligence tools) or other suitable software tools such as a database query software component can be used to help manage and operate community database 32. For example, tools 54 can be used to aggregate patient data from multiple individual patient databases 24. Tools 54 can also be used to process aggregated (community) data to identify patterns and relationships between data. The patterns and relationships that are identified by tools 54 may be used to assist patients in identifying potential errors in their medial expenses.

A patient can access server 16 using patient portal 40. Patient portal 40 can be implemented using any suitable arrangement. With one suitable approach, portal 40 is implemented using a web-based approach, so that patients can use web browsers 14 to access server 16. This is merely an illustrative arrangement. Any suitable interface arrangement may be used to provide the patients with access to the services of data analysis server 16 if desired.

Patient portal 40 may include a query interface 42. The patient may use the query interface 42 to formulate database queries for databases 24 and 32 (e.g., using query engines 31 and 33). Any suitable format may be used when formulating database queries and other commands for operating patient portal 40. For example, patients may be provided with on-screen options such as text-based hyperlinks and buttons on which the patients can click to activate certain associated service features. Patients may also be provided with drop-down menus, text entry boxes (for text commands and data entry), and other suitable graphical user interfaces. Voice commands and annotations may be supported if desired.

Alerts interface 44 may be used to provide alerts to patients. For example, a graphical and/or textual notification may be automatically displayed by a patient's web browser when a condition has been detected by the service that warrants a patient alert.

Claim and statement interface 46 may be used to enter insurance claim and insurance statement information (e.g., to populate databases such as databases 26 and 28).

Private data storage interface 48 may be used to manage a private patient data storage area maintained on server 16. This storage area may be used by a patient to store information of interest to the patient. For example, a patient may store medical articles of interest, scans of interesting documents, to-do lists, and other patient data in the private storage area using interface 48. Interface 48 may be used to support the uploading (transferring) of data from patient computers 12 to server 16 using a suitable communications protocol.

Annotation interface 50 may be used by a patient to attach annotations (comments) to a bill, insurance statement, or other data on server 16. Annotation interface 50 may support typed (text) annotations, handwritten (graphic) annotations, voice annotations (sound clips), and other suitable patient annotation formats.

Configuration interface 52 may be used to by a patient to upload settings for server 16.

Figure 2:
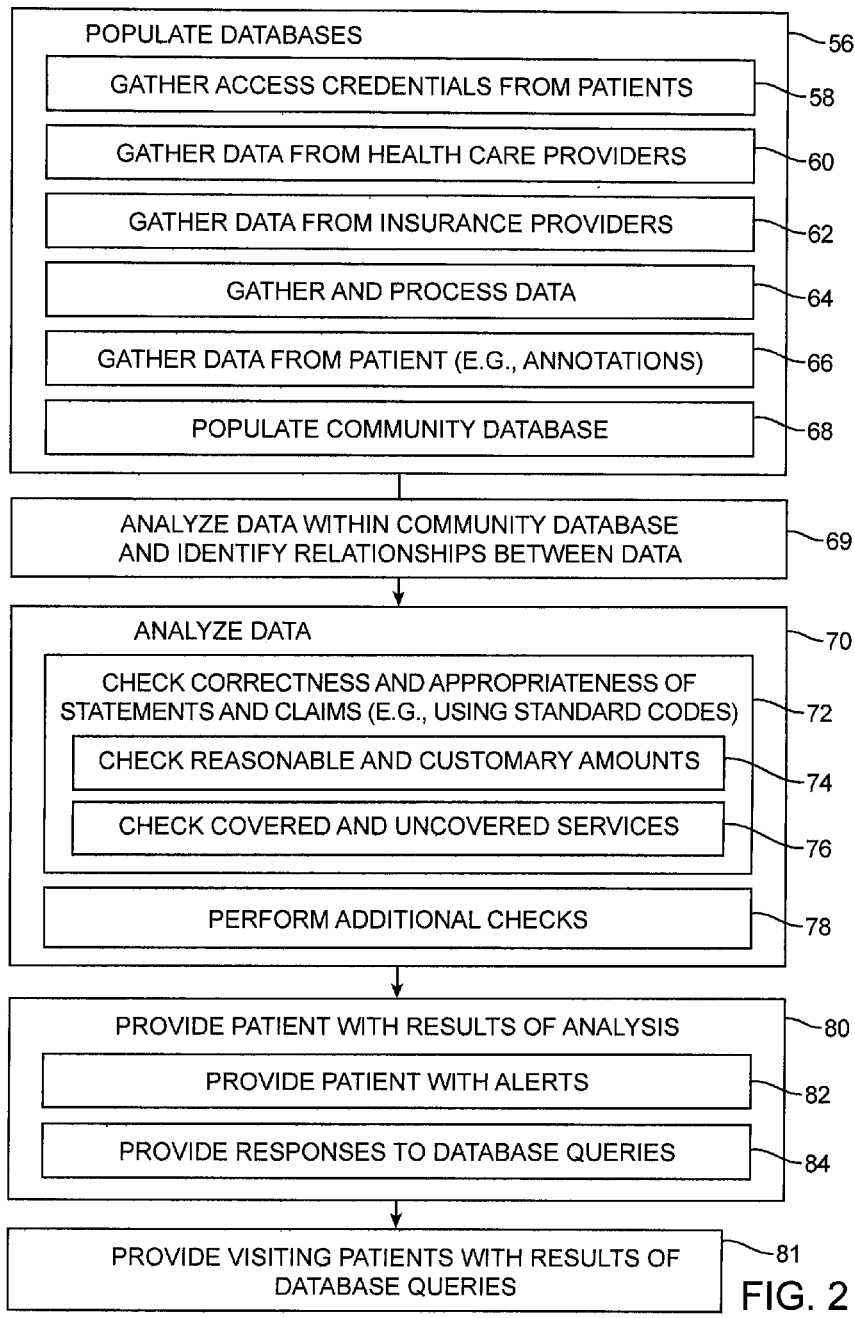
FIG. 2 is a flow chart of illustrative steps involved in using the medical data analysis service of FIG. 1 in accordance with the present invention.

Illustrative steps involved in using the system 10 to assist patients in managing medical expense data and other health care data are shown in FIG. 2. Some of the operations of FIG. 2 are shown as being performed in sequence. This is merely illustrative. In general, the operations of FIG. 2 may be performed concurrently, in other suitable orders, in a looped fashion, in the background (e.g., while other operations are being executed in the foreground), using other suitable approaches, or using a combination of these approaches.

During step 56, patient databases 24 and community database 32 are populated. The operations of step 56 may be performed automatically using the system components of FIG. 1 (with or without manual intervention by a patient and personnel associated with the non-patient entities of FIG. 1).

At step 58, access credentials can be gathered from patients (e.g., through patient portal 40, over the telephone, via fax, by mail, etc.). The access credentials can be used by the data analysis server 16 in automatically gathering copies of health care provider bills from providers 20 and copies of insurance statements from insurance providers 22 over network 18. In a typical scenario, health care providers 20 and insurance providers 22 maintain web-based portals through which patients can access their medical expense data. The health care providers 20 and insurance providers 22 provide web access to only those entities that can provide appropriate credentials. Typically credentials are username and password based, although biometric credentials or other suitable credentials can be used if desired. During step 58, patients can provide server 16 with copies of the usernames and passwords that the patients have at providers 20 and 22.

At step 60, the server 16 can automatically gather data from health care providers 20. If required by health care providers 20, the server 16 can prove that the server 16 is authorized to obtain the requested data by providing the health care providers 20 with appropriate patient access credentials (obtained during step 58). The data obtained during step 60 may include doctor and hospital bills, bills for outpatient services, laboratory bills, and other bills. Bills may be provided in any suitable format (e.g., pixel-based graphics formats, text, combinations of graphics and text, etc.). Billing data from providers 20 need not be comprehensive. For example, a request for a bill may be satisfied by providing the server 16 with data on the bill amount and some or all of the related standardized codes contained in the bill. Not all data fields contained in the bill need be provided to the requesting server 16 (e.g., to preserver privacy, to reduce bandwidth requirements, etc.).

At step 62, the server 16 may gather data from insurance providers 22. Patient access credentials obtained during step 58 may be used to prove that the server 16 is authorized to obtain the requested insurance data. Insurance data may be provided using any suitable data format. Responses to data requests may be satisfied by providing some or all of the contents of a patient's insurance statement data (e.g., codes, reasonable and customary data, deductible and/or co-pay amounts, health care provider charges, previous balance amounts, etc.).

Steps 60 and 62 may be performed automatically (e.g., periodically according to a schedule, each time a patient logs into the service, etc.) or may be performed upon manual instruction from a patient (e.g., an instruction provided to server 16 through patient portal 40).

During step 62, external data may be gathered and processed. The processed external data may be stored in community database 32 as external data 34. Raw external data may be maintained in databases maintained by reliable sources (e.g., databases associated with major medical programs such as Medicaid). The government or private medical entities may maintain such databases. The external databases typically contain information on diagnostic codes and related permitted services (e.g., codes for authorized tests and other medical services that can be reimbursed when performed in response to a particular diagnostic code). Insurance company rules and health care providers rules may also be maintained in these databases. During step 64, server 16 may obtain data from appropriate external databases and may process this data for use in the medical data analysis service. The server 16 may, for example, determine the permitted interrelationships between various diagnoses and associated reimbursable medical services. These relationships and rules may be used by agents 38 and patient intelligence tools 54 to analyze the data in databases 24 and 32 to determine whether a patient has been treated incorrectly or inappropriately by health care providers 20 and/or insurance providers 22.

At step 66, the server 16 can gather data from patients 12. The data that is gathered during step 66 may include annotations such as notes or comments on medical expenses or drug interactions, patient-supplied settings for the service, etc. Patient input may be gathered using patient portal 40 or other suitable techniques.

During step 68, server 16 may populate community database 32. Community database 32 may, for example, be populated by aggregating and processing data from multiple individual patient databases 24. To preserve patient privacy, patients may be required to affirmatively opt in to the data aggregation process before their data is shared. Patient data may also be anonymized prior to inclusion in database 32.

At step 69, server 16 analyzes the data within community database 32 and identifies relationships between data. During step 69, the server 16 may, for example, determine average reasonable and customary amounts from processed data 36 and data from external databases 34. Analysis results may be stored as data 36.

At step 70, server 16 analyzes the data in patient databases 24 and community database 32. During the analysis of step 70, the service can use error detection block 31 in checking to determine whether the patient is being charged unfairly for a medical service by providers 20 and/or insurance providers 22. In particular, during step 72, the server 16 may check the correctness and appropriateness of insurance statements and claims. Standardized billing codes and diagnostic codes may be used by server 16 during this analysis.

As an example, server 16 may check at step 74 to determine whether the "reasonable and customary" amount that a given patient's insurance provider 22 has assigned to a particular procedure is appropriate. The server 16 may make this determination by comparing the given patient's reasonable and customary data (from database 24) with the reasonable and customary data of the relevant portion of community (from database 32). If other patients in the same geographic location as the given patient have received significantly different "reasonable and customary" amounts from their insurers, the given patient may be alerted.

During step 76, the server may check covered and uncovered amounts. For example, server 16 may use information in a patient's database 24 and information in database 32 to determine whether the patient's insurance provider 22 has correctly covered those expenses that should be covered or whether the provider 22 has erroneously indicated that an expense is uncovered when it should have been covered.

Additional checks may be performed by the server 16 during step 78.

Because the data processing operations of step 70 may be performed at server 16 without intervention by health care providers 20 and insurance providers 22, the service of FIG. 1 can identify potential billing and insurance reimbursement problems that affect a patient without regard to the financial interests of health care providers 20 and insurance providers 22. This allows the medical data analysis service to be used to benefit patients.

At step 80, patients may be provided with the results of the data analysis performed at step 70. At step 82, for example, the server 16 may provide appropriate patients 12 with alerts using alerts interface 44. During step 84, patients that have performed database queries may be provided with responses. The database queries may be formulated using any suitable query arrangement (e.g., a natural query language, a query language using particular predefined commands, queries generated using a graphical user interface that allows patients to select from a list of available queries, etc.).

At step 81, patients who are not necessarily subscribers to the medical data analysis service (i.e., visiting patients) may be provided with the results of database queries (i.e., queries performed on database 32 using query engine 33). The results may be provided to a visiting patient with a web browser 14 over communications network 18.

The medical data analysis service described in connection with FIGS. 1 and 2 may be implemented using software running on server 16, software running at health care providers 20 and insurance providers 22 (e.g., to facilitate the automatic population of databases 24 over network 18), and software running at the computing equipment of patients 12 (e.g., web browser software for communicating with server 16 via patient portal 40). The software of the medical data analysis service includes code that configures the hardware of FIG. 1 to perform the operations described in connection with FIGS. 1 and 2. Additional operations may also be performed, as described in more detail below.

The medical data analysis service of the present invention helps patients manage their medical expenses and relieves concerns about the correctness of medical bills and insurance coverage. The service can collects medical expense data for patients without regard to the financial interests of the health care providers 20 and insurers 22, thereby increasing its benefit to patients. The service can transform this data into useful knowledge, which would otherwise not be available to patients. Patients can use the service to compare notes and to correct medical bills and coverage, as well as to make decisions about their health care choices. The service relieves a substantial burden in managing medical expenses and levels the playing field between medical service providers and patients.

As described in connection with FIG. 1, the system 10 may have patient database 24. Each database 24 serves as an individual patient data repository. Databases 24 are used to store provider statements, insurance claims and insurance statements.

There is preferably a patient agent 38 associated with each database 24. Patient agents 38 are software modules each of which acts an expert assistant to manage a patient's medical expenses and which may be used to transform the data in its associated database 24 into more useful information.

Database 32 serves as a collective knowledgebase that is sometimes referred to as a community database or community data warehouse. Database 32 may be populated from individual databases 24 after data has been anonymized. The operations involved in data dissemination from individual patient databases 24 may be restricted based on the consumer's preferences. For example, patients may label certain data as private and other data as shared. These privacy levels can be respected by the server 16 when aggregating data for community database 32.

Patient intelligence tools 54 may be used to discover patterns and relations in the data maintained on server 16. The patterns and relations may be stored in repositories such as databases 24 and 32. A patient can, in general, query both her database 24 and the community database 32. These database queries may be used to uncover information for use in proactive decision making or manual review of medical expenses. The data analysis service may be accessed from anywhere including a computer in a doctor's office (which, in this context would be serving as a patient computer 12), so the patient can stay on top of her medical expenses and choices.

The shared data in community database 32 provides patients 12 with leverage that would otherwise not be available. Large providers 20 and insurance plans 22 collect and analyze patient medical data for the financial benefit of providers 20 and 22. In contrast, the service running on system 10 of FIG. 1 collects and analyzes patient medical expense data independent of the interests of providers 20 and 22, thereby empowering patients.

As described in connection with step 70 of FIG. 2, the medical data analysis service preferably checks the correctness of provider statements. Information on patient insurance claims may be used during these checking operations. The service preferably automates the checking of the correctness and the appropriateness of medical bills and the associated insurance coverage granted to the patient.

Most insurance plans that say they will pay for a percentage of a service (e.g., 80% of an out-of network service) actually pay only a percentage of the "reasonable and customary" service charge, also known as the "allowed amount." This amount is frequently less than the service fee a health care provider 20 charges. The patient is responsible for paying the difference. This required payment is in addition to what the patient needs to pay for the percentage of the allowed amount that insurance does not pay, the co-payment amount, and the applicable deductible.

Without using the service of the present invention, it is difficult or impossible for patients to determine whether a given "reasonable and customary amount" is legitimate. Insurance providers 22 decide on these amounts without any accounting to the patients. In theory, the reasonable and customary amount is based on the amounts other health care providers in a certain geographic area charge for the same service.

In practice, an insurer may sometimes apply reasonable and customary amounts inconsistently. For example, a patient may obtain the same medical service on two separate occasions. On the second of these two occasions, the patient may be assigned a reasonable and customary amount that is significantly less than the amount assigned on the first occasions. Often this type of discrepancy is the result of an honest mistake on the part of the insurance provider. Nevertheless, if the discrepancy is the result of an error and is undetected by the patient, the patient will end up paying more than was appropriate for the first service.

The medical data analysis service uses the patient's medical expense history to detect anomalies such as these. Typically allowable amounts increase over time. The service can use data from the patient's medical expense history to determine how much allowable amounts should increase over time. The service can also consult the aggregated data in community database 32 in making this determination. If desired, the service can be used to enable patients to compare notes with other patients who have had the same service performed within the same geographic area. Patients can therefore compare the reasonable and customary amounts allowed by their insurers. This knowledge gives patients peace of mind when they are treated fairly and provides evidence that can be used to argue for a fair amount when they are treated unfairly.

Patients are often not informed sufficiently when a service is not covered by an insurance provider 22. An exclusion can result from an insurance claim form that has been completed incorrectly by a health care provider 20. Providers 20 typically use standard insurance claim forms and standard codes to describe medical services (diagnostic and treatment procedures and supplies) that have been provided to the patient. For each medical service that is provided, a provider 20 will typically also assign a diagnosis code. The diagnosis code identifies the official diagnosis for the patient's condition that justified performing the medical service. For example, for outpatient claims, a form CMS 1500 is used and CPT™ codes are used to represent the services provided. The CPT codes are used to describe the official diagnoses or medical necessity for performing the medical services for the patient. (CPT is a trademark of the American Medical Association.)

Providers such as hospitals and insurance companies optimize the coding for insurance claims so that their revenues are increased. The service of the present invention provides patients with information that helps clarify the nature of certain charges and whether those charges are appropriate.

A health care provider 20 must generally supply a diagnosis and diagnosis code to support each service. If the provider omits the diagnosis code or supplies an inadequate diagnosis code, the insurance provider 22 will not cover the service. If undetected, the patient will pay for the uncovered service. For example, consider the situation in which a patient visits her doctor for a breast cancer follow-up and complains of chest pain. The doctor performs an ECG. On the claim form, the doctor lists only the ICD-9 code for breast-cancer follow-up. Because it is not clear from the claim for why the ECG was medically necessary, the insurance provider does not pay for the ECG. With the present invention, the medical data analysis service checks for each service code listed on the claim and determines whether there are appropriate diagnostic codes that support the service. The service can alert the patient if the coding is not sufficient to support reimbursement. Moreover, the service can automatically learn from past experience. For example, the service can maintain diagnosis and service relationships that are covered and uncovered, in order to detect mistakes.

The service preferably checks whether the diagnostic codes are consistent with patient's history. For example, the medical necessity for a mammogram is coded in two large categories: diagnostic versus screening. If a patient has a history of breast cancer, her mammogram should be coded in the diagnostic category rather than the screening category. If the code is incorrect, the service can alert the patient.

Exclusion of a service can also result from insurers' inconsistencies. An insurance provider might claim that a service is unnecessary even if there is appropriate medical necessity. For example, the insurer might claim that an MRI is too aggressive and that instead a more conservative X-ray should have been performed for a bone fracture. As a result, the insurer might only reimburse the patient for an X-ray amount. The medical data analysis service preferably checks the histories in the patient's database 24 and the community database 32 to determine whether there are situations in which the disputed service was covered under the same medical necessity. This knowledge provides the patient with peace of mind or the power to argue for fair coverage.

In some situations, an insurance provider 22 might exclude services if the health care provider 20 does not follow the insurer's guidelines when fill in a claim form. For example, if a health care provider might submit a claim containing CPT service codes that are not supposed to used together. As another example, an insurance plan might require, on a CMS-1500 form, the following for a mammogram service: "On item 24E, enter the diagnosis code reference number (1, 2, 3, or 4) from item 21 to relate the date of service and the procedures performed to the primary diagnosis listed. Only reference one diagnosis indicator in item 24E, per line of service from the valid diagnosis codes in item 21." If multiple reference numbers are entered on item 23E, the insurer might not cover the service. If this mistake is undetected, the patient is held responsible for the service amount. The medical data analysis service learns (and maintains) these rules and checks whether claims comply with them.

The health care services provided to a patient are fragmented. Numerous different entities are typically involved in the health care of a patient. A patient generally has a choice between different in-network and out-of-network providers for her medical, dental, mental health and vision services. It is desirable to have choices for health care, but the multiplicity of providers makes patients' financial accounting more difficult. Similarly, each patient is typically enrolled with multiple health benefit plans. Commonly, primary medical, vision, dental, mental health care and prescription drug benefits are offered by different insurance plans. As a result, the patient receives a separate statement from each provider and from each insurance plan. The same provider might have different billing departments leading to more statements. For example, a hospital may have separate billing departments for inpatient services, outpatient services and physician services. Similarly, visiting a doctor's private practice might lead to separate bills from different labs. The numerous statements involved in these situations introduce more sources of potential errors and other issues.

For some patients, the process of understanding even a single provider or insurance statement is difficult. Quite often a statement consists of multiple services and the patient does not know whether these services are appropriate or not. Even a seemingly single service (such as a doctor visit or a test) can lead to multiple codes for services, procedures, supplies, and treatments. An example is a CT scan. When a CT scan is performed, a patient will be charged for the CT scan procedure and for the radiologist who will read the CT scan separately. Furthermore, if the patient had a CT scan in a hospital, the CT scan procedure will appear on the outpatient statement while radiology service will appear on the physician's statement.

Many medical services are dependent on the existence of other services (e.g., a radiologist service listed on a physician statement for reading a CT scan depends on the existence of a CT scan procedure on the outpatient or lab statement). The patient is not always aware of the service dependencies and therefore does not understand whether the services she is charged for are appropriate. The service of the present invention is provided with information on service dependencies when populating the databases on server 16. During operation, the service can continue to "learn" more about service dependencies. The analysis service can automatically uses the service dependencies to confirm the appropriateness of the medical services. The analysis service may also learn and use referral dependencies of medical services to justify the medical services. The data analysis service also confirms when medical services that have been provided are within the specialization of a provider (e.g., by using codes).

A provider, particularly one supplying multiple types of services, might submit an insurance claim to the wrong insurance plan (e.g., by sending the claim for a psychologist visit to the primary medical insurance rather than the mental health insurance). A provider might also either forget to send a claim or send it to the wrong policy number.

If any of these mistakes goes undetected, the services will not be properly covered and the patient will be responsible for the full amount of the service. The data analysis service of the present invention detects these types of mistakes by tracking related events on different provider and insurance statements.

The data analysis service also checks whether insurance policies are applied consistently to a given medical service.

Each insurance policy has rules that govern how a service will be covered. For example, besides the deductibles and co-pays for an in-network service, there are typically rules such as "if an in-network provider sends a test to an external lab because the provider does not have the resources, the external lab's services should be considered in-network." Similarly, there are rules specifying how an out-of network service is covered (at least the specification of allowed amount, co-pay, deductible, percentage of the allowed amount covered up to maximum out-of-packet), and how negotiated services will be covered. The rules can be entered through the patient portal 40 and/or learned over time. For example, the employer of a patient may ask for a special arrangement between an insurance provider 22 and a psychologist, so that the psychologist charges a fraction of his fee. This rule can be provided to the service through the patient portal 40.

The data analysis service preferably tracks provider statements to ensure that the payments for the service both from the insurer and the patient are used appropriately. It also tracks fees for similar services to make a judgment how the fee requested by the provider compares.

Providers 20 use standard codes (e.g., ICD-9, CPT) to communicate with insurers 22. These codes contain information that can be transformed into useful knowledge for the patient. However, even raw information from these codes is not conventionally utilized by patients. One of the main reasons for this is that the patient is (rightfully) not an expert in complex coding and in medical terminology. Furthermore, the patient does not want to know all the raw information encoded in the coding, but what is important to her, when this information makes a difference or when she needs it.

The data analysis service of the present invention preferably uses the standard diagnostic and service codes. Using standard coding, the service verifies the appropriateness and correctness of patient's medical expenses and insurance coverage for the patient, independent of the financial interests of the health care providers and the insurers. The service can derive useful knowledge for the patient (again independent from the interests of the providers and insurers) from the raw coding and terminology used in insurance claims and provider and insurance statements. The service connects the pieces of information encoded in separate claims, statements, and annotations into knowledge which is otherwise not available to the consumer.

Patient databases 24 and database 32 are preferably populated with data from provider statements, insurance statements and insurance claims that can be transformed into useful information for checking medical claims and insurance statements. The data in databases 24 and 32 can be queried by the patient to gain insights on medical expenses.

The data analysis service preferably enables patients to annotate data in databases 24. This allows patients to maintain comments and notes.

The following are few query examples that may be performed on the medical expense data that has been collected and the knowledge that has been mined from the expense data:

How much did my condition diabetes cost me this year? Because the analysis service learns and keeps track of medical service, diagnosis and referral dependencies, the analysis service can calculate the total cost of procedures, medical services, supplies and treatments due to diabetes and the other conditions it leads to. This type of knowledge can be used, for example, to decide whether to buy a supplemental health insurance policy or on a specified or dread-disease policy.

How much did I pay out-of pocket in the year 2005? The patient can use this knowledge to decide whether and how much to contribute to health accounts like pre-tax reimbursement accounts.

How much did I pay out-of packet in year 2005 for services performed in 2005 or before? List these services. This information can be used for filing a 2005 tax return.

How much was the total cost of dental care in the last five years? How much of this amount have I paid out-of pocket? How much did I spend in dental care premiums? This information is helpful in deciding whether to enroll in a dental insurance plan next year.

How much is the total cost of an X-ray at a given provider? Because the data analysis service keeps track of service dependencies, the answer will cover not only the X-ray procedure but also the radiologist reading.

The medical data analysis service preferably enables patients to learn not only from their own medical expenses data, but also from the collective knowledge derived from other patients' medical expense data and corresponding annotations and comments. The variety of knowledge available to the patient may be significantly more valuable than if the patient is restricted to using only her own data.

Examples include the following:

What is the reasonable and customary amount in Manhattan for a first dermatologist visit? Typically, the consumer does not have enough information to make proactive decisions about her health care choices. The patient prefers to go to an out-of network specialist, but does not know whether she can afford it. Even if she learns the doctor's fee in advance, she may not know what her insurance will designate as the reasonable and customary amount until she visits the doctor, submits the insurance claim and receives the corresponding insurance statement. The data analysis service enables consumers to make proactive decisions about their health care choices.

How much is the total cost of chemotherapy for a breast cancer patient at Memorial Sloan Kettering? Because the data analysis service tracks medical service, diagnosis and referral dependencies, it will also account for the cost of blood tests, oncologist visits, bone-scans, etc. How much of this would be covered by my insurance? How much would I pay if I go to an in-network provider? This knowledge enables the consumer to decide whether she can afford to be treated at a top cancer center or whether she needs to use an in-network provider.

What is the total cost of breast cancer follow-up in the three years following surgery, chemotherapy and radiation? Because the data analysis service tracks service, diagnosis and referral dependencies, it will detect the cost of colonoscopy, mammogram, ultrasound, bone-scans, etc. that are required for breast cancer follow-up. This information can be used to decide on insurance coverage over the years. For example, this information may be used to choose a deductible amount that will reduce the insurance premium or to make policy choices that will avoid lifetime limits paid under an insurance policy.

The data analysis system preferably identifies patterns and relationships or interest in the data stored in databases 24 and 32. For example, consider an illustrative pattern: significant number of patients who received weekly treatment of chemotherapy drugs fluorouracil, epirubicin and cyclophosphamide were hospitalized for lung problems during or short time after this treatment. Such a pattern is not only interesting for health reasons but also to project patients' medical expenses more accurately. The cost of an emergency room visit can be factored into the overall cost of for the given chemotherapy therapy.

Are there breast cancer patients with a given insurer who had PET scans and are PET scans covered by this insurer? If so, what was the attributed medical necessity?

How many times does a breast cancer patient go to the emergency department while she is undergoing chemotherapy?

What are the medical diagnoses for these emergency visits?

What new diagnostic and preventive tests and treatments do others use for breast cancer?

Is there anyone who had microarray gene testing? If so, how much did it cost? What are the patient's notes?

How does my yearly medical spending compare to other breast cancer patients?

Are there patients in NY with a particular insurance plan who underwent ovary removal with an in-network provider? What are their comments on the provider? Are any of these providers part of any "official ratings?"

What are the top three complaints of women whose ovaries have been removed because of ovarian cysts with no known risk to cancer and when they were premenopausal?

A patient has numerous mental or written notes about services, providers, drugs, supplies, therapies, etc. Even with computer-stored notes, it can become difficult or impossible to remember and utilize these notes effectively. The data analysis service of the present invention provides annotation services that allow patients to remember, find, connect and make use of notes.

For example, if a patient stops taking a drug (Arimidex™) and her severe heartburn and acid reflux disappear, she may query the databases at server 16 to ask "after which drug did I start complaining about heartburn?". She may learn that the heartburn and acid reflux started after she had started to take Arimidex. She may then conclude that these were the side effects of Arimidex.

The data analysis service enables patients to annotate each the data in databases 24. In the present example, the patient could annotate the right instance of the drug data type to store her belief about the Arimidex' side effects. This information will also be useful for fellow patients who are taking the same drug.

The annotations are not only useful to write comments on providers, services, etc., but also to connect patient's own notes with the services in a coherent way: e.g., notes from a doctor visit (what the doctor told her), questions to a doctor, complaints and symptoms before a doctor's visit, and logs of complaints. The data analysis service enables patients to connect, analyze and utilize these annotations in a cohesive way.

A stage 3 breast-cancer patient, after surgery, chemotherapy and radiation, is recommended the classical breast-cancer follow-up by her oncologist, which is visiting an oncologist every six months and having blood tests. A nightmare of breast cancer patients is metastasis. However, oncologists typically do not order scans or other tests to detect metastasis early, unless the patient has clinical symptoms. This patient visits one of the top cancer centers to get a second opinion on the follow-up. They recommend that she should have scans every year even without any symptoms. The data analysis service of the present invention enables the patient to annotate her database with this information to share it with others. Besides supporting queries for this type of information, the data analysis service can generate alerts to remind the patient of this information.

The system 10 preferably uses an architecture that includes individual patient databases 24, one for each patent. There is preferably a patient agent 38 associated with each database 24, each of which manages a patient's medical expenses and database 24. The community database 32 is used to maintain knowledge gathered from patients using the service.

Patient intelligence software tools 54 can be used by patients and patient agents 38 for data analysis and decision support.

The patient portal 40 (also sometimes referred to as a consumer interface) preferably contains a number of interfaces 42, 44, 46, 48, 50, and 52, as shown in FIG. 1.

Portal 40 allows a patient to read and query all the data in his patient database 24. Preferably, the service places restrictions on what the patient can write and change in his patient database 24. As we describe below, a patient preferably cannot change data that has been electronically collected from providers 20 and 22.

The patient agent 38 transforms raw data collected from a patient 12 and providers 20 and 22 into useful information, which can be stored in the patient's database 24. The patient cannot change this data, although the patient can query the data using the query interface 42 and using patient intelligence tools.

The patient can also query the community database 32. The patient is preferably not allowed to write or change the data in the community database 32, which may be populated with data through the patient databases 24 under the guidance of their associated patient agents 38. Patients can also access community data through intelligence tools 54.

The alert interface 44 enables patients to observe and react to the alerts generated by corresponding patient agents 38.

Patients are also provided with an interface 50 to support annotation of the different pieces of data in their patient databases 24 and to allow patients to write comments on medical services, providers, and drug side effects.

Patients can use the claim and statement interface 46 for entering statement and claim data (e.g., for statements and claims that are not collected electronically) and for entering other medical expenses such as non-prescription drugs or transportation to treatment. Structured online forms are provided to simplify the entry for provider statements, insurance claims and insurance statements.

Within each database 24, a patient may be provided with private storage that the patient can use to store data of interest. This area can be structured as a remote file directory with a typical file system interface. Other patients and their corresponding patient agents 38 preferably cannot access a patient's private storage. The patient might store, for example, a file with his to-do notes in this area.

The configuration interface 52 provides tools for entering rules for insurance policies, accounts like pre-tax reimbursement accounts, special agreements and a patient's restrictions on data migration to the community warehouse. A structured online form may be provided to simplify the entry.

Each patient is preferably provided with a separate database 24 and has access to only his own database. Each patient database 24 is used to collect and organizes medical expense data for the patient and to make it available for analysis and querying.

Data acquisition operations may be performed from various sources, including the patient's health care providers and insurance provider. Data acquisition may be performed electronically over network 18. Acquired data may be represented using any suitable data structures. For example, acquired data may be provided in the form of provider statements, insurance claims and insurance statements. Data can also be entered manually by authorized personnel such as the patient. The patient preferably cannot alter data that has been gathered electronically from providers and insurers. The consumer is preferably provided with a structured interface similar to the statement and claim forms to enter the relevant data when necessary.

Each piece of data used to populate databases 24 and 32 may be marked to indicate its source. This enables analysis and management tools in the service such as agents 38 and tools 54 to assess the quality of data and take the necessary cautions to use differently marked data. For example, a manually entered fee for a service can be suspected of potential error. However, if this service later appears in an insurance claim, the data analysis service can upgrade the marking of the data to indicate its probable correctness.

Databases 24 may archive raw data from provider statements, insurance claims, and insurance statements. Although the same medical service can appear on consecutive statements without any state change, the data analysis service preferably stores the data so that the statements can be regenerated with the same appearance as if gathered from an original source. Maintaining versions and history is important for supporting rebuttals, learning trends (e.g., how long it takes to finalize a claim for a given service) and analysis.

A patient may have other sources of medical expenses, which are important to track even if they are not covered by insurance. Examples include non-prescription drugs, transportation to treatments, and extra wigs for chemotherapy patients. The patient can enter this type of expense through the interface 46 as another provider statement.

Each patient database 24 is preferably associated with a corresponding patient agent 38 that manages the correctness of the statements and claims. The agent 38 can also consolidate and transform raw data from statements and claims into more useful information over time. Thus, the database 24 preferably stores not only collections of unprocessed of statements and claims but also the transformed data on the patient's medical expenses. This information can be queried by the patient, but preferably cannot be changed by the patient. The data analysis service preferably provides an interface to the patient to annotate different pieces of data in his database 24.

The following are some of the data types that are typically generated:

Service: The attributes of the service data type are: service date, service type, service code, medical necessity, medical necessity code, provider, referred by, service fee, insurance plan, adjusted (negotiated) fee, reasonable and customary amount, excluded amount by the insurance, exclusion reason, type of insurance coverage (e.g., out-of network, in-network), co-pay, deductible, percentage of the allowed amount paid by insurance, the amount patient is responsible for, user comments, the date service charge is resolved, personal assistant notes.

Diagnosis and service relationship: Diagnosis type, diagnosis code, service type, service code, frequency of service, covered (covered, partially covered, not covered), covered elsewhere, insurer notes, personal assistant notes, and a link to the corresponding service instance.

Service dependency: A directed graph. The nodes are service types. A directed edge denotes that the sink node depends on the existence of source node.

Referral dependency: A directed graph. The nodes are service types. A directed edge denotes that the sink node is referred by the source node.

Patient medical history: A directed graph with nodes representing the diagnosis and labeled edges denoting relationships such as occurred before, occurred together, and associated with.

Patient service history: A directed graph with labeled edges denoting relationships such as occurred before, occurred together, referred by, and depends on. The nodes are service instances.

Inconsistency: This data type tracks the instances of errors the personal assistant detected.

Pattern: This data type tracks interesting patterns discovered by the intelligence tools within the patient databases.

The data attributes are populated over time and their values may change over time. Some attributes may not be available at all. Attributes themselves can be compound data types, such as provider and insurance plan. While the raw data from statements and claims is preferably processed to turn it into various other data types, the marking of data indicating its source is preferably maintained.

A patient is generally allocated private data storage as part of his database. This space may be structured as a remote file directory and may only be accessible by the patient. The patient agent and other software components are generally not allowed to access the private storage.

Each patient agent 38 reviews, analyses and evaluates the "correctness" of health care provider statements, insurance claims and insurance statements collected in a patient database 24. The agent 38 preferably oversees a medical service until the medical service is resolved over time. When the agent detects a problem, the agent generates alerts. The alerts may trigger reevaluation of charges, coverage and reimbursement. During this process, the patient agent transforms raw data stored in the database 24 into more useful information. It also oversees when and what information to be sent to the community database 32.

The patient agent 38 learns about new medical services from provider statements, insurance claims or insurance statements. The term "medical service," which is sometimes used to refer to the services listed in medical billing forms, can also be used to refer to medical procedures, supplies and treatments.

For each medical service, the agent 38 gathers the attributes listed above for the service data type. This is done over time, because provider statements, insurance claims and insurance statements arrive at different times. A service can also show up in consecutive statements and claims due to delays until the insurance provider 22 finalizes a claim or until the patient pays the amount for which he is responsible, or due to multiple rounds between a billing department and the insurance provider to handle adjustments. As a result, the state of the medical service changes over time. The patient agent 38 preferably tracks these state changes while observing each medical service across multiple statements and claims until the medical service is resolved (i.e., until there are no open issues left about concerning the charges for the medical service, the coverage, and the patient's responsibility, and the patient has paid his responsibility).

Standard coding (e.g., ICD-9 and CPT) and standard insurance claims simplify the data schema integration. The number attributes are not large. Medical terminology dictionaries may be used if desired for schema integration.

On arrival of a new provider statement, insurance claim or insurance statement, the appropriate patient agent 38 checks for correctness. If the agent detects any problems, the agent may generates an alert or alerts.

The following are some of the potential problems the agents 36 may evaluate:

For each provider statement and insurance claim:
Are the services charged to the right insurance?
Is the coding for services and diagnoses appropriate?
Is the insurance claim form completed consistent with the insurer's guidelines?
Are the services appropriate?
Are the requested fees for services appropriate?
Are the patient's payments used appropriately?
For each insurance statement:
Is the amount allowed by the insurance provider appropriate?
Are excluded services and amounts appropriate?
Is the insurance policy implementation correct (are the deductible, co-insurance, and insurance payment correct?)

These evaluations are executed incrementally over time, because they generally involve using the patient agent 36 to evaluate previous and future statements and claims in addition to querying the databases 24 and 32. Consider the evaluation of whether a service is submitted to the right insurance. The health care provider statements do not necessarily contain enough information to detect this problem immediately. For example, the physician billing department of a hospital might send a charge for a psychologist service to the primary insurance of a patient rather than to his mental health insurance. The provider statement will show the full service fee under the category "pending insurance amount." The primary insurance will not pay. After a couple of provider statements, the patient's responsibility will be changed to the full service fee. Just looking at the consecutive provider statements, there will not be enough information to decide whether the claim was not submitted at all, was submitted to the wrong insurance plan, or was submitted to the right insurance plan which did not cover the service. Accordingly, the patient agent preferably checks statements from different insurance plans in addition to the provider statements to determine the problem.

The patient agent can also perform cross-checks between an insurance statement and a provider statement to ensure that the medical services listed in both statements match and so do their fees and coverages. These types of cross-checks are simpler to implement. The main issue for these types of cross-checks are consolidation of the data scheme of different statements. On the other hand, scheme integration for billing purposes is simpler than in other domains due to the presence of fewer items, clues such as service dates, and standard coding.

The patient agent 38 preferably learns over time the details of a service, different service and diagnosis relationships that are covered and not covered, the patient's medical history, service dependencies, referral relationships and other patterns and relationships. The agent uses this knowledge and the similar knowledge in the community database 32 to check the statements and claims.

The patient can enter insurance policy rules using patient portal 40. The patient agent 38 preferably learns the rules for each policy over time. The patient may be provided with a structured form to enter health accounts such as a pre-tax reimbursement account. The patient agent manages this account so that the out-of packet medical payments, which are already reimbursed from an account are not used for other reimbursements or tax deductions.

The patient agent preferably manages alerts. An alert may result from a state change in the statements or from an action of the patient. The patient agent may make the patient aware of alerts through alerts interface 44.

The patient agent also preferably keeps track of inconsistencies it has detected and stores them in the patient database.

Besides querying the database and the community database, the patient agent also may use the patient intelligence tools 54 for data review, data analysis and new pattern identification operations.

Under the supervision of a corresponding patient agent 38, selected data from each patient database is provided to the community database 32. This data may be anonymized before it is stored in database 32. The community database 32 preferably integrates the collected data from the various patient databases 24 and prepares the collected data for analysis and querying. The community database 32 is used by the patient agents, by patients, and by the patient intelligence tools 54 to compare notes, perform queries, mine information of interest, learn, and make decisions.

Similar data types to the medical service, diagnosis and service relationship, medical service dependency, referral dependency, and patient medical and service histories, as described for a patient database, are also maintained in the community database 32. However, in database 32, this information is preferably linked anonymously to a patient. The patient agent may omit certain data values before sending data from a patient database 24 to the community database 34 in accordance with patient preferences. For example, the provider attribute might be cut short and only the specialization and the geographic location might be passed to the community database to preserve privacy.

The patient agent 38 also maintains insurance claim data type information. Most providers use standard insurance claim forms, which dictates which data attributes are involved. For each insurance claim, the community warehouse will collect as much information as possible. Examples of attributes that the agent collects for an insurance claim are: the type of the insurance claim form (e.g., CMS 1500), the diagnostic codes, the service codes, service dates, service fees, provider name, referred by information, and insurance company name. The data is preferably linked anonymously to a patient. These data attributes are populated over time and their values change over time. Some attributes may not be available at all. The patient agent sends updates to reflect changes.

The community database 32 is preferably used not only to collect and integrate data from different patient databases 24, but to derive new knowledge from collected data. Each piece of data is preferably marked based on its source. This enable the database 32 to differentiate the quality of data and take the necessary precautions when generating new knowledge. Patient intelligence tools are used to derive new patterns and relationships, which are stored back in the database 32.

The service and diagnosis relationships data (external data 34) can be obtained from external databases and can be updated and otherwise extended from the knowledge learned from patients' medical expenses.

The community database 32 can be populated and maintained without regard to the interests of health care providers 20 and insurance providers 22. Database 32 can be used to provide knowledge to patients that would otherwise not be available. This empowers patients who are managing their medical expenses.

The medical data analysis service preferably includes tools such as tools 54 that allow aggregations to be performed over multiple dimensions and that support operations related to statistics, drill-downs and drill-ups, and data mining to find patterns of interest within the data.

The results of these tools can be stored in the community database 32 where they can be queried by the patients 12 and patient agents 38. If desired, tools such as tools 54 can be used on demand by the patient and the patient agents to gain new insights and perspectives.

The following are few examples for the associations and patterns that can be discovered by patient intelligence tools 54 such as data mining tools.

A significant number of patients who received weekly treatment of chemotherapy drugs fluorouracil epirubicin and cyclophosphamide were hospitalized for lung problems during or short time after this treatment.

A significant number of patients who were admitted to the hospital for a primary diagnosis encoded with a given DRG code are admitted again for the same reason within two months.

A significant number of ECGs performed during doctor visits were initially covered by insurance because the insurance claim did not have a supporting diagnosis.

Such patterns are not only interesting for health reasons but also to project medical expenses more accurately. For example, if the community database is asked, how much the overall cost of a given chemotherapy therapy is, the cost of emergency room visit can be listed as potential cost.

The medical data analysis service provides patients with a powerful tool for managing their health care expenses. During setup operations, patient data regarding medical expenses (bill amounts, coverage amounts, etc.) is obtained and stored in the patient databases 24. The patient medical expense data may be obtained by extracting the data from records that are available to the patient and/or by enabling the patient to enter data manually (e.g., using web browsers 14). During data analysis operations, the service analyzes patient data to detect billing errors (e.g., insufficient insurance coverage due to erroneous "reasonable and customary" amounts, insufficient insurance coverage due to incorrectly denied services, etc.). The patient medical data that is maintained in the patient databases includes data for multiple health care organizations (e.g., multiple insurance companies, multiple health care providers, etc). The service allows patients to search for stored records. Patients can track expenses by reviewing stored records and can perform calculations on stored data to assist in making health care expenditure decisions.

Using the community database functions of the service, patient medical care data can be stored including medical expense data (e.g., data on bill amounts, coverage amounts, etc.) Medical data can be maintained private by anonymizing the data. The service may analyze community data and can make the results of this analysis available to patients.

If desired, the service may provide multiple levels of functionality. For example, basic community database search features may be provided to public users (e.g., users who desire to browse the service over the internet). Higher-level functionality (e.g., medical expense data error checking) may be performed for users who have subscribed with the service.

Data may be acquired for the data analysis server using any suitable technique. For example, records that are available to a patient or that have been sent to the patient that relate to her health care expenses and benefits (e.g., the statements from providers, statements from health saving accounts, explanation of benefits from insurances, claims from providers or insurances, and other related documents) may be gathered automatically by the service (e.g., over communications network 18) or may be entered manually (e.g., by using a web browser to provide this information to data analysis server 16).

The service may use any suitable naming and indexing scheme to facilitate easy storage and searching of documents. The values used for naming attributes may be automatically extracted from patients' documents or may be manually entered by a patient or other authorized person.

A user of the service may modify or enhance the values of attributes that have been automatically extracted by the service. The patient or the service may manually or automatically tag medical expense documents with clues (e.g., keywords) that assist the service in categorizing the documents.

The service may acquire medical expense data during step 56 of FIG. 2 using any suitable technique. For example, documents such as account statements and bills may be provided to a patient as a paper copy, by email, or online (e.g., as a download from a health care organization's web site). Paper documents may be scanned and uploaded to data analysis server 16. Scanning and uploading may be performed by a patient (directly or through an assistant) or by the personnel at the medical data analysis service. Documents that contain medical expense data that a patient has received via email may be forwarded to the data analysis server 16. Documents available online can be directly downloaded by the server 16.

A patient's health care records may contain redundant information or information about a transaction (i.e., a medical expense transaction related to a medical event and associated medical service) that is changing over time. It can be challenging, for a patient to track transactions simply by viewing the relevant documents. The medical data analysis service addresses this challenge, because the medical data analysis service can extract transactions from databases 24. For example, the service may extract data on medical services and health savings account reimbursements. The service may maintain the latest state of each transaction. The attributes and information that are maintained for each transaction are extracted by the service from patient medical data documents. A patient may enhance or otherwise modify extracted data (e.g., by adding annotations). As an example, entries related to a medical service can appear in multiple insurance and health care provider statements. The attribute values associated with the entries may be the same or may vary. The medical data analysis service can extract data for a given medical service from multiple provider statements and can maintain the associated attribute values up to date.

The medical data analysis service may map medical services appearing on a health care provider statement with the corresponding medical services appearing on an explanation of benefits document from an insurance provider. This mapping may be complex. For example, both documents may refer to a service with a different name, a service that has been identified as a single service by the health care provider may be separated into multiple services by the insurance provider, multiple services that are identified individually by a health care provider may be collapsed into a single service by the insurance provider, the name used for the same health care provider may be different on health care provider and insurance provider documents, etc.

Moreover, a patient or health care provider may submit a claim to multiple insurance providers, e.g., primary insurance and secondary insurance. The medical data analysis service preferably maps a health care item that appears in a health care provider statement to the corresponding services appearing on multiple explanation of benefit documents from different insurance providers.

In order to automatically retrieve medical expense data and other data from medical documents and to perform mapping functions for related transactions, the medical data analysis service preferably uses medical and billing coding and terminology standards. Electronic data exchange standards may also be used. The medical data analysis service may learn different ways of mapping from the history of our users as well as from other reputable sources.

In addition to information on medical services, the medical data analysis service may maintain information for providers, patients, insurance companies and other parties involved in caring for patient health. Such information may be collected automatically from documents, from other patients' records, and from reputable data sources.

During the mapping operations performed by the medical data analysis service, the medical data analysis service may identify relationships between medical service events. For example, a medical service may be requested by the provider of another service (i.e., as part of a referral or recommended test). A medical service may also be a follow-up to another service or may otherwise be a consequence of a previous service. The medical data analysis service analyses the medical expense data and other data in databases 24 to discover the relational model between services. By discovering the relational model between services, a detailed medical history may be produced for a patient and the medical data analysis service. The medical data analysis service may determine the relationships between services via the use of coding, terminology standards, and patient data.

The medical data analysis service may detect mistakes and inconsistencies in a patient's medical bills, provider statements, and insurance provider explanation of benefits documents. The medical data analysis service may analyze a patient's own data to detect errors, may analyze data from reputable sources (e.g., Medicare databases) to detect errors, and may analyze collective data that has been gathered from multiple patients to detect errors.

The medical data analysis service alerts patients about detected errors in the medical expense data. The medical data analysis service also enables the patient to enter notes and to annotate documents and other records. For example, a patient can annotate data that has been extracted from medical expense documents with his own notes. The medical data analysis service enables the patient to search through these notes and annotations.

The medical data analysis service may use medical coding, billing coding, and terminology standards to relate data (e.g., similar services, similar diagnosis, similar history, similar provider, similar geography) from different patients. During data analysis operations, the medical data analysis service may detect relationships between different services, diagnosis and history. The relationships that are detected may form patterns. The patient may be informed of detected patterns. The medical data analysis service allows patients to share and search each other's notes and annotations. For example, patients can annotate their own data and add notes and can share notes and annotations with other users of the service.

The service may gather and analyze data from reputable external sources (e.g., Medicare databases and expert question boards) to enhance the collective knowledge of the community of patients that are using the service. Each piece of data may be labeled by the medical data analysis service based on its source. Labeling information may be used to indicate the importance of each data item for use when analyzing data or when presenting search results. When this type of approach is used, the data analysis server gathers data for the user-searchable database from external databases including Medicare databases and labels the gathered data with labeling information based on its source. The labeling information is then used in evaluating the importance of data when analyzing the data and when presenting data to the user over the communications network. Taking into account the importance of data in this way allows the service to assign a greater weight to reliable sources of information.

The foregoing is merely illustrative of the principles of this invention and various modifications can be made by those skilled in the art without departing from the scope and spirit of the invention.

What is claimed is:

1. A method for allowing a given patient to manage health care expenses using a computer-implemented medical expense data analysis service, comprising:
   receiving health care provider statements from multiple health care providers and explanation of benefits documents from multiple insurance providers after patient responsibilities have been determined by the multiple health care providers and the multiple insurance providers;
   with the computer-implemented medical expense data analysis service, checking medical expense data for the given patient that is associated with multiple insurance providers and multiple health care providers to detect billing and coverage errors, wherein the billing and coverage errors include mistakes and inconsistencies in the health care provider statements and the insurance provider explanation of benefits documents, and wherein checking the medical expense data comprises automatically discovering patterns and relationships in the medical expense data with data mining techniques;
   maintaining at least one patient database containing the patient medical expense data and data on detected billing and coverage errors;
   allowing the given patient to query the patient database; and
   alerting the given patient to the identified billing and coverage errors.

2. The method defined in claim 1 further comprising:
   with at least one data analysis server associated with the medical expense data analysis service, maintaining multiple patient databases that include medical expense data for multiple patients from multiple insurance providers and multiple health care providers;
   at the data analysis server, analyzing the medical expense data for the multiple patients and multiple insurance providers and multiple health care providers in the patient databases to check for errors in the medical expense data of the given patient;
   at the given patient, using a web browser to access the data analysis server over a communications network; and
   using the web browser to provide the given patient with results from analyzing the medical expense data with the data analysis server that indicate whether the medical expense data of the given patient contains errors.

3. The method defined in claim 2 wherein the medical expense data comprises data from patient health care provider statements and insurance company explanation of benefits forms and wherein analyzing the medical expense data comprises analyzing the data from the health care provider statements and explanation of benefits forms.

4. The method defined in claim 3 wherein analyzing the data from the health care provider statements and explanation of benefits forms comprises determining whether there are deficiencies in coverage provided by any of the insurance providers for the given patient or whether there are errors in charges from any of the health care providers for the given patient.

5. The method defined in claim 2 wherein analyzing the medical expense data comprises:
   analyzing data from external databases including a Medicare database.

6. The method defined in claim 2 wherein analyzing the medical expense data comprises:
   analyzing data collected from multiple patients who use the medical expense data analysis service.

7. The method defined in claim 2 further comprising gathering medical expense data annotations from patients who use the medical expense data analysis service using the web browser and the data analysis server.

8. The method defined in claim 2 further comprising:
   at the data analysis server, acquiring data that includes the medical expense data by acquiring the health care provider statements from the health care providers and the explanation of benefits forms from the insurance providers; and
   building an index for maintaining the medical expense data at the data analysis server, wherein building the index comprises automatically extracting attributes from the health care provider statements and from the explanation of benefits forms and accepting manual data entry from patients.

9. The method defined in claim 8 further comprising:
   at the data analysis server, extracting transactions from documents including the statements from health care providers and the explanation of benefits forms from insurance providers, wherein when a medical service appears in a plurality of the documents with changing attribute values, the data analysis server extracts the attribute values for the medical service from the documents and maintains a latest set of the extracted attribute values.

10. The method defined in claim 2 wherein the medical expense data comprises medical expense data obtained from documents that have been sent to patients as paper documents, documents that have been sent via email, and documents that are available online to download, the method further comprising:
    scanning and uploading the paper documents to the data analysis server;
    forwarding email documents to the data analysis server; and
    at the data analysis server, directly downloading the documents that are available online.

11. The method defined in claim 10 further comprising:
    at the data analysis server, extracting transactions from documents including the statements from health care providers and the explanation of benefits forms from insurance providers, wherein when a medical service appears in a plurality of the documents with changing attribute values, the data analysis server extracts the attribute values for the medical service from the documents and maintains a latest set of the extracted attribute values.

12. The method defined in claim 2 wherein the medical expense data includes medical services that appear on the health care provider statements, the method further comprising:
    using the data analysis server to map medical services that appear on a given health care provider statement for the given patient with corresponding services appearing on multiple explanation of benefits documents from multiple insurance providers for the given patient.

13. The method defined in claim 2 wherein the medical expense data comprises medical expense data for related medical services and wherein the related medical services include medical services resulting from referrals, medical services that are follow-ups to previous medical services, and medical services that are a consequence of previous medical services, the method further comprising using the data analysis server to determine relationships between the related medical services using medical and billing coding standards.

14. A method for allowing patients to obtain health care information using a computer-implemented medical expense data analysis service, comprising:
   anonymizing and analyzing patient medical expense data of multiple patients from multiple insurance providers and multiple health care providers to produce anonymized and analyzed patient medical expense data;
   with at least one data analysis server associated with the medical expense data analysis service, maintaining a searchable community database of the anonymized and analyzed patient medical expense data;
   in response to a given patient of the multiple patients using a web browser to access the searchable community database at the data analysis server over a communications network, automatically comparing the medical expense data of the given patent with the medical expense data of other patients in the searchable community database; and
   providing to the given patient results of the comparison of the medical expense data of the given patient with the medical expense data of the other patients in the searchable community database.

15. The method defined in claim 14 wherein anonymizing and analyzing the patient medical expense data at the data analysis server comprises using medical and billing coding standards to identify relationships in the patient medical expense data in which patients have used similar medical services and have had a similar diagnosis.

16. The method defined in claim 14 wherein anonymizing and analyzing the patient medical expense data at the data analysis server comprises using medical and billing coding to identify relationships in the patient medical expense data in which patients have used different medical services, had a different diagnosis, and have had different medical histories.

17. The method defined in claim 14 further comprising using the data analysis server to allow patients to share and search each other's notes and annotations.

18. The method defined in claim 14 further comprising using the data analysis server to gather data for the searchable community database from external databases including Medicare databases.

19. The method defined in claim 14 further comprising:
   using the data analysis server to gather data for the searchable community database from external databases including Medicare databases;
   labeling data gathered for the searchable community database with labeling information based on its source; and
   using the labeling information in evaluating the weight of data when analyzing the data and when presenting data to the given patient over the communications network.

20. A method for allowing a given patient to manage health care expenses using a computer-implemented medical expense data analysis service, comprising:
   with at least one data analysis server associated with the medical expense data analysis service, maintaining multiple patient databases that include medical expense data for multiple patients from multiple insurance providers and multiple health care providers, wherein the multiple patients include the given patient;
   at the data analysis server, analyzing the medical expense data for the multiple patients from multiple insurance providers and multiple health care providers from the multiple patient databases to check for errors in the medical expense data of the given patient, wherein analyzing the medical expense data comprises automatically discovering patterns and relationships in the medical expense data with data mining techniques;
   at the given patient, using a web browser to access the data analysis server over a communications network;
   using the web browser to provide the given patient with results from analyzing the medical expense data with the data analysis server that indicate whether the medical expense data of the given patient contains errors;
   anonymizing and analyzing the medical expense data in the multiple patient databases for the multiple patients from multiple insurance providers and multiple health care providers to produce anonymized and analyzed patient medical expense data;
   at the analysis server, maintaining a searchable community database of the anonymized and analyzed patient medical expense data;
   in response to the given patient using a web browser to access the searchable community database at the data analysis server over a communications network, automatically comparing the medical expense data of the given patent with the medical expense data of other patients in the searchable community database.

21. The method defined in claim 1, further comprising:
   with the computer-implemented medical expense data analysis service, checking medical expense data for a plurality of patients that are associated with multiple insurance providers and multiple health care providers to detect billing and coverage errors that are associated with each patient in a plurality of patients, wherein checking the medical expense data comprises automatically discovering patterns and relationships in the medical expense data with data mining techniques;
   maintaining a plurality of patient databases, wherein each patient in the plurality of patients has an associated database in the plurality of databases that contains medical expense data and data on detected billing and coverage errors;
   allowing each patient to query its associated patient database; and
   alerting each patient to its associated identified billing and coverage errors.

22. The method defined in claim 21, further comprising:
   anonymizing the medical expense data and the data on detected billing and coverage errors from each of the patient databases in the plurality of patient databases to produce anonymized medical expense data and anonymized data on detected billing and coverage errors;
   maintaining the anonymized medical expense data and anonymized data on detected billing and coverage errors in a community database; and
   allowing each patient in the plurality of patients to query the community database.

* * * * *